United States Patent

Brieden et al.

[11] Patent Number: 5,939,549
[45] Date of Patent: Aug. 17, 1999

[54] PROCESS FOR THE PRODUCTION OF 1,4,5, 6-TETRAHYDROPYRAZINE-2-CARBOXYLIC ACID AMIDES

[75] Inventors: Walter Brieden, Glis; Jean-Paul Roduit, Grône; Rudolf Fuchs, Sion, all of Switzerland

[73] Assignee: Lonza AG, Gampel/Valais, Switzerland

[21] Appl. No.: 08/860,713

[22] PCT Filed: Jan. 19, 1996

[86] PCT No.: PCT/EP96/00223

§ 371 Date: Jul. 11, 1997

§ 102(e) Date: Jul. 11, 1997

[87] PCT Pub. No.: WO96/22981

PCT Pub. Date: Aug. 1, 1996

[30] Foreign Application Priority Data

Jan. 23, 1995 [CH] Switzerland ............... 178/95
Dec. 6, 1995 [CH] Switzerland ............... 3443/95

[51] Int. Cl.⁶ ................................................. C07D 241/06
[52] U.S. Cl. ............................................................. 544/406
[58] Field of Search ........................ 544/406, 388

[56] References Cited

U.S. PATENT DOCUMENTS

| 4,734,449 | 3/1988 | Gugumus | 524/328 |
| 4,734,499 | 3/1988 | Hickman | 544/336 |
| 5,413,999 | 5/1995 | Vacca et al. | 514/252 |
| 5,463,067 | 10/1995 | Askin et al. | 548/113 |
| 5,612,484 | 3/1997 | Askin et al. | 544/360 |
| 5,663,341 | 9/1997 | Rossen et al. | 544/388 |
| 5,723,615 | 3/1998 | Rossen et al. | 544/388 |
| 5,734,055 | 3/1998 | Watanabe et al. | 544/406 |

FOREIGN PATENT DOCUMENTS 0175364  3/1986  European Pat. Off. .
0541168  5/1993  European Pat. Off. .
0744401  11/1996 European Pat. Off. .
96-194600 6/1996  WIPO .

OTHER PUBLICATIONS

Fuchs et al. Chem. Abstr. vol. 126 entry 47240 abstracting EP 744 401, 1996.
Doye et al. Chem. Abstr vol. 128 entry 34787, 1997.
Felder, E., et al., Helv. Chim. Acta, 43, (1960), 888–896.
Rossen, K., et al., Tetrahedron Letters, vol. 36, No. 36, pp. 6419–6422 (1995).

*Primary Examiner*—John M. Ford
*Attorney, Agent, or Firm*—Fisher, Christen & Sabol

[57] ABSTRACT

A process for the production of 1,4,5,6-tetrahydropyrazine-2-carboxylic acid amides of the general formula (I), where $R^1$ means hydrogen, alkyl, cycloalkyl or arylalkyl, $R^2$ means alkyl, aryl or arylalkyl and $R^3$, $R^4$ and $R^5$ mean independently from each other hydrogen, alkyl, aryl or arylalkyl or $R^2$ forms an alicyclic system with $R^3$ or $R^4$ and the adjacent C atom(s), $R^6$ being hydrogen or acyl. The products are obtained from the corresponding tetrahydropyrazine carboxylic acid nitriles and olefins or corresponding carbenium ion precursors and possibly carboxylic acids in a Ritter reaction. The products are new and can be used, for example, for the production of piperazine carboxylic acid amides.

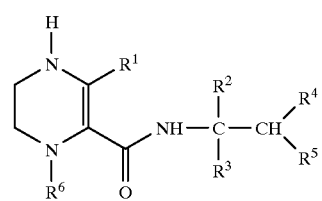

(I)

16 Claims, No Drawings

PROCESS FOR THE PRODUCTION OF 1,4,5,6-TETRAHYDROPYRAZINE-2-CARBOXYLIC ACID AMIDES

The present invention relates to a process for preparing 1,4,5,6-tetrahydropyrazine-2-carboxamides of the general formula

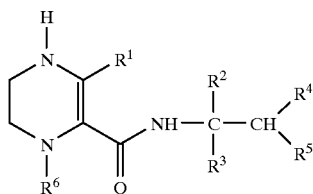

I where $R^1$ is hydrogen, a $C_1$–$C_{30}$-alkyl radical, a cycloaliphatic radical having 3 to 8 ring members, an aromatic radical or an araliphatic radical having 7 to 12 carbon atoms, and (a) $R^2$ is a $C_1$–$C_6$-alkyl radical, an aryl radical or an arylalkyl radical and $R^3$, $R^4$ and $R^5$ independently of one another are each hydrogen, $C_1$–$C_6$-alkyl radicals, aryl radicals or arylalkyl radicals, or (b) $R^2$ joins with $R^3$ or $R^4$ and the adjacent carbon atom(s) to form a mono- or polycyclic alicyclic system which may optionally be substituted by one or more $C_1$–$C_4$-alkyl groups, and $R^5$ and $R^4$ or $R^3$ are each as defined above, and $R^6$ is hydrogen or a group of the formula $R^7$—C(=O)— where $R^7$ is hydrogen or optionally substituted $C_1$–$C_6$-alkyl.

Here and below, alkyl radicals are in each case straight-chain or branched primary, secondary or tertiary alkyl groups, i.e. for example methyl, ethyl, propyl, isopropyl, butyl, sec-butyl, tert-butyl, isobutyl, pentyl, isopentyl, neopentyl, hexyl, octyl, etc.

Substituted alkyl is for example alkoxyalkyl groups or haloalkyl groups, in particular perfluoroalkyl groups such as, for example, trifluoromethyl.

Cycloaliphatic radicals are cycloalkyl groups, i.e. for example cyclopropyl, cyclobutyl, cyclopentyl, cyclohexyl, etc.

Aryl radicals or aromatic radicals are mono- or polycyclic aromatic groups which may optionally be substituted by $C_1$–$C_4$-alkyl groups or halogens, i.e. for example phenyl, 1-naphthyl, 2-naphthyl, o-tolyl, m-tolyl, p-tolyl, xylyls, chlorophenyls, etc.

Correspondingly, arylalkyl radicals or araliphatic radicals are aryl-substituted alkyl radicals, in particular benzyl, 1-phenylethyl or 2-phenylethyl.

It is known that pyrazinecarboxylic acids and derivatives thereof such as esters and amides can be hydrogenated using heterogeneous catalysts (for example Pd/C). However, this hydrogenation usually leads to the corresponding piperazine derivative, i.e. the heteroaromatic ring becomes fully hydrogenated. Partial hydrogenation to the tetrahydropyrazine system has only been observed in exceptional cases, in which the isolation of a pure product in the case of the tetrahydropyrazinecarboxylic esters caused problems and the corresponding amide was not obtainable by this route. (E. Felder et al., Helv. Chim. Acta, 1960, 43, 888–896).

It is an object of the present invention to provide an industrial route to 1,4,5,6-tetrahydropyrazine-2-carboxamides substituted at the amide nitrogen. These previously unknown compounds are to provide alternative access to the corresponding piperazinecarboxamides, of which for example the (S)-piperazine-tert-butylcarboxamide is a building block of an active compound for the treatment of AIDS (U.S. Pat. Nos. 5,413,999, 5,527,799, 5,668,132 and 5,717,097)

According to the invention, this object is achieved by the process of of the invention and the compounds of of the invention.

It has been found that the 2-cyano-1,4,5,6-tetrahydropyrazines of the general formula

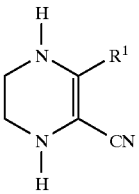

II where $R^1$ is as defined above, react in the presence of a strong acid with compounds of the general formula

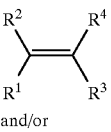

IIIa and/or

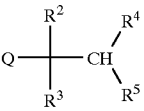

IIIb where $R^2$, $R^3$, $R^4$ and $R^4$ are each as defined above and Q is a group which can be removed to leave a carbenium ion, in a Ritter reaction. It is probable that in this reaction a nitrilium salt is initially formed by the addition of the carbenium ion, formed from IIIa by protonation and/or from IIIb by removal of the group Q, to the cyano group, the nitrilium salt then being hydrolysed to the amide. If the reaction is carried out in the presence of a carboxylic acid of the formula

$$R^7\text{—COOH} \qquad \text{IV}$$

where $R^7$ is as defined above, position 1 of the tetrahydropyrazine ring is additionally selectively acylated, affording a product (I) where $R^6$=$R^7$—C(=O)—. Without the addition of a carboxylic acid, the corresponding compound where $R^6$=H is obtained. The embodiment with the addition of a carboxylic acid is preferred, since the acyl group may act as a protecting group in subsequent syntheses, permitting selective reactions at the nitrogen atom in position 4.

Particular preference is given to using carboxylic acids where $R^7$ is hydrogen, a $C_1$–$C_3$-alkyl group or a $C_1$–$C_3$-perfluoroalkyl group, in particular acetic acid ($R^7$=$CH_3$) or trifluoroacetic acid ($R^7$=$CF_3$).

Suitable 2-cyano-1,4,5,6-tetrahydropyrazines according to formula II are those having hydrogen in position 3 ($R^1$=H) and those having $C_1$–$C_{30}$-alkyl radicals, cycloaliphatic radicals having 3 to 8 ring members, aromatic radicals or araliphatic radicals having 7 to 12 carbon atoms.

These compounds are easily obtainable from α-dicarbonyl compounds, ethylenediamine and cyanide by the process described in European Published Patent Application No. 0175364 and U.S. Pat. No. 4,734,499. Preference is given to using the compound which is unsubstituted in position 3 ($R^1$=H).

Additionally, it has been found that corresponding compounds which already carry an acyl group in position 1 (at the nitrogen atom) surprisingly do not participate in the reaction of the invention at all, or only to a very small extent, although they should afford the same products. On the other hand, it has been found that even under drastic conditions (excess of carboxylic acid, presence of thionyl chloride) selective $N^1$-acylation occurs, and that virtually no $N^1,N^4$-diacylated products are obtained.

The 2-cyano-1,4,5,6-tetrahydropyrazines (II) can be employed as free bases and as salts. Suitable salts are in particular the monosalts with strong acids, for example the hydrohalides, the hydrogen sulfate or the sulfonates. Compared with the free bases, these salts also have the advantage of a better storage stability. Particular preference is given to the monomethanesulfonate.

Suitable strong acids in the reaction medium are correspondingly the so-called mineral acids, such as, for example, sulfuric acid, phosphoric acid and perchloric acid, sulfonic acids such as, for example, methanesulphonic acid, benzenesulfonic acid or polymeric sulfonic acids (acidic ion exchangers), strong carboxylic acids, such as, for example, formic acid or trifluoroacetic acid, or else Lewis acids, such as, for example, boron trifluoride. Particular preference is given to methanesulfonic acid.

Suitable compounds of the formulae IIIa and IIIb are alkenes (IIIa) and also compounds which can form carbenium ions on removal of a group Q under the action of a strong acid (IIIb).

Suitable alkenes are open-chain alkenes where $R^2$ is a $C_1$–$C_6$-alkyl radical, an aryl radical or an arylalkyl radical and $R^3$, $R^4$ and $R^5$ independently of one another are each hydrogen, $C_1$–$C_6$-alkyl, aryl or arylalkyl, and also cyclic alkenes. In the cyclic alkenes, the double bond may be exocyclic, so that $R^2$ joins with $R^3$ and the adjacent carbon atom to form a mono- or polycyclic alicyclic system, or it may be endocyclic, so that $R^2$ together with $R^4$ and the two adjacent carbon atoms forms a mono- or polycyclic alicyclic system. Examples of open-chain alkenes are propene, 1-butene, 2-butene, isobutene, the various isomeric pentenes and hexenes, styrene, alkylbenzene and stilbenes.

Alkenes having an exocyclic double bond are, for example, methylenecyclohexane or the bicyclic camphene. Alkenes having an endocyclic double bond include, for example, the cycloalkenes, such as cyclopentene, cyclohexene and cycloheptene.

A particularly preferred alkene (IIIa) is isobutene ($R^2$=$R^3$=$CH^3$, $R^4$=$R^5$=H).

Of the compounds (IIIb) which afford carbenium ions on removal of a group Q in the presence of strong acids, the alcohols (Q=OH) and derivatives thereof, such as, for example, esters (Q=acyloxy) or ethers (Q=alkoxy) are of particular importance. Isopropyl and tert-butyl alcohol, methyl tert-butyl ether, tert-butyl acetate and cyclohexanol may be mentioned as examples.

Of course, the invention also includes the joint use of alkenes (IIIa) with the corresponding compounds of the formula IIIb, i.e. for example isobutene together with tert-butyl alcohol.

The reaction conditions depend on the starting materials employed and can be varied within wide limits. The acid itself, i.e. for example sulphuric acid or the carboxylic acid (IV) which is optionally added, can serve as solvent, but it is also possible to add further polar or apolar inert solvents.

The reaction temperature is advantageously in the range of 0–50° C., preferably 15–30° C.

It is advantageous to avoid high concentrations of alkene (IIIa) or of the compound IIIb in the reaction mixture, so as not to favor the formation of polymers and oligomers. To this end, the alkene or the compound IIIb is not precharged but added slowly at the rate of the reaction.

Work-up can be carried out by conventional methods, for example by extracting the optionally neutralized reaction mixture. In many instances, the product formed precipitates after basic work-up and can be separated off by filtration or centrifugation.

The following examples illustrate the practice of the process according to the invention.

EXAMPLES

Example 1

1-Acetyl-1,4,5,6-tetrahydropyrazine-2-tert-butylcarboxamide

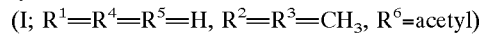

At room temperature, 70 g (0.77 mol) of methanesulfonic acid and then 20.0 g (184 mmol) of 2-cyano-1,4,5,6-tetrahydropyrazine were added slowly to 100 ml (1.75 mol) of acetic acid. At 25° C., 23.0 g (410 mmol) of isobutene were passed into this mixture, and the mixture was stirred for 5 h.

With cooling, the mixture was then neutralized using 30% strength aqueous sodium hydroxide solution, the temperature at all times being kept below 30° C. The mixture, which had been adjusted to pH 8–10, was extracted three times with 200 ml of methyl ethyl ketone each time. The combined organic phases were dried over magnesium sulphate and the solvent was distilled off. The residue (41.2 g) was dissolved in 80 ml of hot ethyl acetate. After cooling to 20° C., 500 ml of hexane were added, the mixture was cooled further to 0° C. and the precipitated product was filtered off after 1 h and dried.

Yield: 32.6 g (79%) of a light-beige powder m.p.: 151.3–152.6° C.

$^1$H NMR ([$D_6$]DMSO, 400 MHz): δ=1.27 (s, 9H) 1.89 (s, 3H); 3.06–3.12 (m, 2H); 3.31–3.40 (m, 2H); 6.46 (br. s, 1H); 6.59 (br. s, 1H); 6.80 (d, J=7.2 Hz, 1H).

Example 2

1-Acetyl-1,4,5,6-tetrahydropyrazine-2-tert-butylcarboxamide

Similarly to Example 1, 22 g (0.23 mol) of methanesulfonic acid and 10 g (92 mmol) of 2-cyano-1,4,5,6-tetrahydropyrazine were added to 30 ml of acetic acid and 20 ml of water, and 8.65 g (154 mmol) of isobutene were passed in.

After the reaction had ended, the mixture was neutralized with 119 g of 30% strength aqueous sodium hydroxide solution at 5° C. and adjusted to pH 11.6. The precipitated product was filtered off, washed with 10 ml of ice-water and dried under reduced pressure.

Yield: 28.9 g of a light-yellow powder having a content of 58% (equivalent to 80% of theory).

Example 3

1-Propionyl-1,4,5,6-tetrahydropyrazine-2-tert-butylcarboxamide

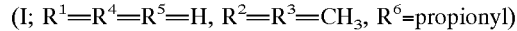

The compound was prepared similarly to Example 1 using propionic acid instead of acetic acid.

Yield: 75% m.p.: 172.4–172.6° C.

¹H NMR (CDCl₃, 400 MHz): δ=1.09 (t, J=7.3 Hz, 3H); 1.37 (s, 9H); 2.39 (q, J=7.3 Hz, 2H); 3.28 (m, 2H); 3.57 (m, 2H); 5.41 (br. s, 1H); 5.49 (br. s, 1H); 7.09 (d, J=6.3 Hz, 1H)

¹³C NMR (CDCl₃, 100 MHz): δ=9.44 (CH₃); 27.55 (CH₂); 29.12 (CH₃); 38.29 (CH₂); 42.19 (CH₂); 50.92 (C); 106.66 (C); 132.20 (CH); 165.21 (C=O); 177.20 (C=O).

Example 4

1-Isobutyryl-1,4,5,6-tetrahydropyrazine-2-tert-butylcarboxamide (I; R¹=R⁴=R⁵=H, R²=R³=CH₃, R⁶=isobutyryl)

The compound was prepared similarly to Example 1 using isobutyric acid instead of acetic acid.

Yield: 48% m.p.: 180.0–184.4° C.

¹H NMR (CDCl₃, 400 MHz): δ=1.07 (d, J=6.5 Hz, 6H); 1.37 (s, 9H); 2.82 (sept, J=6.5 Hz, 1H); 3.27 (m, 2H); 3.6 (br. m, 2H); 4.94 (br. s, 1H); 5.48 (br. s, 1H); 7.12 (d, J=6.3 Hz, 1H).

¹³C NMR (CDCl₃, 100 MHz): δ=19.36 (CH₃); 29.07 (CH₃); 32.50 (CH); 38.39 (CH₂) 42.42 (CH₂); 50.94 (C); 106.73 (C); 132.07 (CH); 165.21 (C=O); 180.85 (C=O).

Example 5

1-(Methoxyacetyl)-1,4,5,6-tetrahydropyrazine-2-tert-butylcarboxamide (I; R¹=R⁴=R⁵=H, R²=R³=CH₃, R⁶=methoxyacetyl)

The compound was prepared similarly to Example 1 using methoxyacetic acid instead of acetic acid.

Yield: 52% m.p.: 185.5–189.9° C.

¹H NMR (CDCl₃, 400 MHz): δ=1.38 (s, 9H); 3.33 (m, 2H); 3.41 (s, 3H); 3.59 (m, 2H); 4.17 (s, 2H); 5.12 (br. s, 1H); 5.47 (br. s, 1H); 7.11 (d, J=6.3 Hz, 1H).

¹³C NMR (CDCl₃, 100 MHz):=29.12 (CH₃); 38.27 (CH₂); 42.11 (CH₂); 51.09 (C); 59.31 (CH₃O); 70.86 (CH₂O); 105.48 (C); 132.72 (CH); 164.53 (C=O); 172.39 (C=O);

Example 6

1-Trifluoroacetyl-1,4,5,6-tetrahydropyrazine-2-tert-butylcarboxamide (I; R¹=R=R⁴=R⁵=H, R²=R³=CH₃, R⁶=trifluoroacetyl—from the methanesulphonic acid salt of 2-cyano-1,4,5,6-tetrahydropyrazine)

Under argon, 50 ml of trifluoroacetic acid were precharged in a 500 ml flask. At 21° C., 12.5 g of methanesulfonic acid were added dropwise, and 20 g of the methanesulphonic acid salt of 2-cyano-1,4,5,6-tetrahydropyrazine (97 mmol) were then added a little at a time, a slightly exothermic reaction being observed. Within 1 h, 10 g (178 mmol) of isobutene were then added at 20° C. The reaction mixture was stirred for a further 2 h at 20° C. and then, at this temperature, admixed dropwise with 13.3 g (111 mmol) of thionyl chloride and stirred for a further 20 h. 250 ml of dichloromethane and, a little at a time, 25 g of sodium acetate were then added. After the crude solution was filtered through Celite®, 30 ml of water were added and the phases were separated. The organic phase was evaporated to dryness. The remaining crude product (27.88 g) was chromatographed over 300 g of silica gel using ethyl acetate/methanol (4:1).

Yield (GC): 29.2% m.p.: 158.–160° C. (from n-butyl acetate).

¹H NMR (CDCl₃, 400 MHz) : δ1.35 (s, 9H); 3.43 (br. s, 2H); 3.74 (br. s, 2H); 5.32 (br. s, 1H); 5.53 (br. s, 1H); 7.06 (d, J=6 Hz, 1H).

¹³C NMR (CDCl₃, 100 MHz): δ=28.9; 42.3; 42.8; 51.2; 105.9; 116.3 ($J_{C-F}$=288 Hz); 133.2; 154.5 ($J_{C-F}$=35 Hz); 163.7.

MS: m/z=57 (100%), 279 (M⁺, 6.2%).

Comparative Example

Attempted preparation of 1-acetyl-1,4,5,6-tetrahydropyrazine-2-tert-butylcarboxamide from 1-acetyl-2-cyano-1,4,5,6-tetrahydropyrazine A) ¹-Acetyl-2-cyano-1,4,5,6-tetrahydropyrazine 10.0 ml (106 mmol) of acetic anhydride and 8.0 ml (99 mmol) of pyridine were added to 5.10 g (47 mmol) of 2-cyano-1,4,5,6-tetrahydropyrazine, and the mixture was stirred at 20° C. for 18 h. After aqueous work-up, the reaction product was extracted three times with 100–200 ml of ethyl acetate each. The combined organic extracts were dried over magnesium sulphate and concentrated. The crude product was then purified by flash chromatography (silica gel 40×3 cm, ethyl acetate:hexane=4:1, $R_f$=0.25). the fraction having $R_f$=0.25 (5.82 g) was taken up in 40 ml of diethyl ether and the precipitated solid was filtered off and dried.

m.p.: 100.5–102.0° C. Yield: 5.62 g (80%) of a slightly yellow solid

NMR data:

The rotation of the acetyl group around the amide bond is strongly hindered, so that separate signals for the two possible conformers (E and Z form) of a ratio of intensities of 3:2 are obtained in the NMR spectrum. Here, the two conformers are labelled A and B, the letter A being assigned arbitrarily to the conformer present in a greater amount.

¹H NMR ([D₆]DMSO, 400 MHz):

Conformer A: δ=2.15 (s, 3H); 3.14–3.20 (m, 2H); 7.09 (d, J=7.0 Hz, 1H); 7.46 (br. s, 1H).

Conformer B: δ 2.01 (s, 3H); 3.25–3.33 (m, 2H); 6.90 (d, J=7.0 Hz, 1H); 7.01 (br. s, 1H).

Conformer A+B: δ=3.44–3.56 (m, 2+2H) ¹³C NMR ([D₆]DMSO, 100 MHz):

Conformer A: δ=22.38 (CH₃); 80.67 (C); 119.48 (C≡N); 138.59 (CH); 168.50 (C=O).

Conformer B: δ=20.97 (CH₃); 81.94 (C); 118.35 (C≡N); 137.16 (CH); 166.65 (C=O).

Assignment unclear: δ=36.17 (CH₂); 41.45 (CH₂); 41.69 (CH₂); 41.74 (CH₂).

B) Attempted reaction with isobutene

At 20° C., 4.91 g of 1-acetyl-2-cyano-1,4,5,6-tetrahydropyrazine (32.5 mmol) were added to a solution of 12.73 g of 98% strength sulphuric acid (130 mmol) in 50 ml of glacial acetic acid. Over 3 h, 3.62 g of isobutene (64.5 mmol) were passed through the solution at a constant temperature, and the reaction mixture was then stirred for a further 3 h. The dark brown suspension was poured onto 106 g of ice and adjusted to a pH 8 with 30% strength aqueous sodium hydroxide solution at T<20° C. A fine precipitate (Na₂SO₄) was filtered off and the filtrate was continuously extracted with dichloromethane overnight. Only a little black solid was isolated by evaporating the organic phase. The aqueous phase was concentrated. The solid residue was suspended in 80 ml of boiling ethanol, about ⅔ of the amount dissolving. Evaporation gave 6.8 g of an orange solid. This was taken up in hot isopropanol and the insoluble part was filtered off. 3.52 g of 1-acetyl-1,4,5,6-tetrahydropyrazine-2-carboxamide crystallized from the isopropanol solution as a beige solid (64% yield).

¹H NMR ([D₆]DMSO, 400 MHz):δ=1.92 (s, 3H); 3.10 (m, 2H); 3.35 (m, 2H); 6.60 (br. s, 2H); 6.72 (br. s, 1H); 7.00 (d, J=6.3 Hz, 1H).

¹³C NMR ([D₆]DMSO, 100 MHz):δ=25.39 (CH₃); 36.89 (CH₂); 41.51 (CH₂); 105.37 (C); 131.96 (CH); 166.66 (C=O); 170.33 (C=O).

We claim:
1. Process for preparing 1,4,5,6-tetrahydropyrazine-2-carboxamides of the formula:

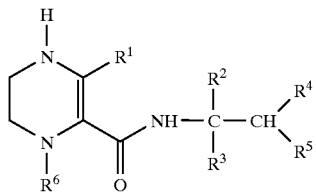

I where $R^1$ is hydrogen, a $C_{1-30}$-alkyl radical, a cycloaliphatic radical having 3 to 8 ring members, a monocyclic aromatic radical which may optionally be substituted by $C_{1-4}$-alkyl groups or halogens, or an aryl-substituted alkyl radical having 7 to 12 carbon atoms, where aryl is monocyclic, 1-naphthyl or 2-naphthyl,
(a) $R^2$ is a $C_{1-6}$-alkyl radical, an aryl radical where aryl is monocyclic, 1-naphthyl or 2-naphthyl, which may optionally be substituted by $C_{1-4}$-alkyl groups or halogens, or an aryl-substituted alkyl radical, where aryl is monocyclic, 1-naphthyl or 2-naphthyl, and $R^3$, $R^4$ and $R^5$ independently of one another are each hydrogen, $C_{1-6}$-alkyl radicals, aryl radicals, where aryl is monocyclic, 1-naphthyl or 2-naphthyl, or aryl-substituted alkyl radicals, where aryl is monocyclic, 1-naphthyl or 2-naphthyl, or
(b) $R^2$ joins with $R^3$ or $R^4$ and the adjacent carbon atom(s) to form a mono- or alicyclic system which may optionally be substituted by one or more $C_{1-4}$-alkyl groups, and $R^5$ and $R^4$ or $R^3$ are each as defined above, and $R^6$ is hydrogen or a group of the formula $R^7$—C(=O)— where $R^7$ is hydrogen or optionally substituted $C_{1-6}$-alkyl,
characterized in that a 2-cyano-1,4,5,6-tetrahydropyrazine of the formula:

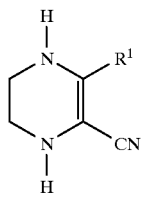

II where $R^1$ is as defined above, or a salt thereof, is reacted in the presence of a strong acid with a compound of the formula:

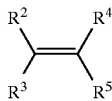

IIIa where $R^2$, $R^3$, $R^4$ and $R^5$ are each as defined above, and optionally with a carboxylic acid of the formula:

$$R^7—COOH \qquad IV$$

where $R^7$ is as defined above, and the resulting nitrilium compound is hydrolyzed to the amide (I).

2. Process according to claim 1, characterized in that the reaction of the 2-cyano-1,4,5,6-tetrahydropyrazine (II) with the compound IIIa is carried out in the presence of a carboxylic acid (IV) and a 1-acyl-1,4,5,6-tetrahydropyrazine-2-carboxamide (I) where $R^6$ is a group of the formula $R^7$-C(=O)— is obtained.

3. Process according to claim 2, characterized in that the carboxylic acid used is acetic acid or trifluoroacetic acid.

4. Process according to claim 3, characterized in that the 2-cyano-1,4,5,6-tetrahydropyrazine used is 2-cyano-1,4,5,6-tetrahydropyrazine which is unsubstituted in position 3 ($R^1$=H).

5. Process according to claim 4, characterized in that the 2-cyano-1,4,5,6-tetrahydropyrazine is employed in the form of the monomethanesulfonate.

6. Process according to claim 5, characterized in that the strong acid used is methanesulfonic acid.

7. Process according to claim 6, characterized in that the compound of the formula IIIa used is isobutene.

8. Process according to claim 1, wherein the 2-cyano-1,4,5,6-tetrahydropyrazine used is 2-cyano-1,4,5,6-tetrahydropyrazine which is unsubstituted in position 3 ($R^1$=H).

9. Process according to claim 8, wherein the 2-cyano-1,4,5,6-tetrahydropyrazine is employed in the form of the monomethanesulfonate.

10. Process according to claim 1, wherein the strong acid used is methanesulfonic acid.

11. Process according to claim 1, wherein the compound of the formula IIIa used is isobutene.

12. Process according to claim 1, characterized in that $R^1$ is phenyl, 1-naphthyl, 2-naphthyl, o-tolyl, m-tolyl, p-tolyl, a xylyl or a chlorophenyl.

13. Process according to claim 1, characterized in that $R^2$ is phenyl, 1-naphthyl, 2-naphthyl, o-tolyl, m-tolyl, p-tolyl, a xylyl or a chlorophenyl .

14. Process according to claim 1, characterized in that $R^1$ is benzyl, 1-phenylethyl or 2-phenylethyl.

15. Process according to claim 1, characterized in that $R^2$ is benzyl, 1 -phenylethyl or 2-phenylethyl.

16. Process for preparing 1 -acetyl- 1,4,5,6-tetrahydropyrazine-2-tert-butylcarboxamide, comprising reacting 2-cyano-1,4,5,6-tetrahydropyrazine in the presence methanesulfonic acid with isobutene and with acetic acid to produce a nitrilium compound, and hydrolyzing the nitrilium compound to the product.

* * * * *